US00PP16828P2

(12) United States Plant Patent
Pierce

(10) Patent No.: US PP16,828 P2
(45) Date of Patent: Jul. 18, 2006

(54) ***CALIBRACHOA* PLANT NAMED 'CAL BRITREEDA'**

(50) Latin Name: ***Calibrachoa* sp.**
Varietal Denomination: Cal Britreeda

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 97 days.

(21) Appl. No.: 11/090,460

(22) Filed: Mar. 25, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

A *Calibrachoa* cultivar particularly distinguished by its large red flowers and small leaves is disclosed.

1 Drawing Sheet

Figure 1:
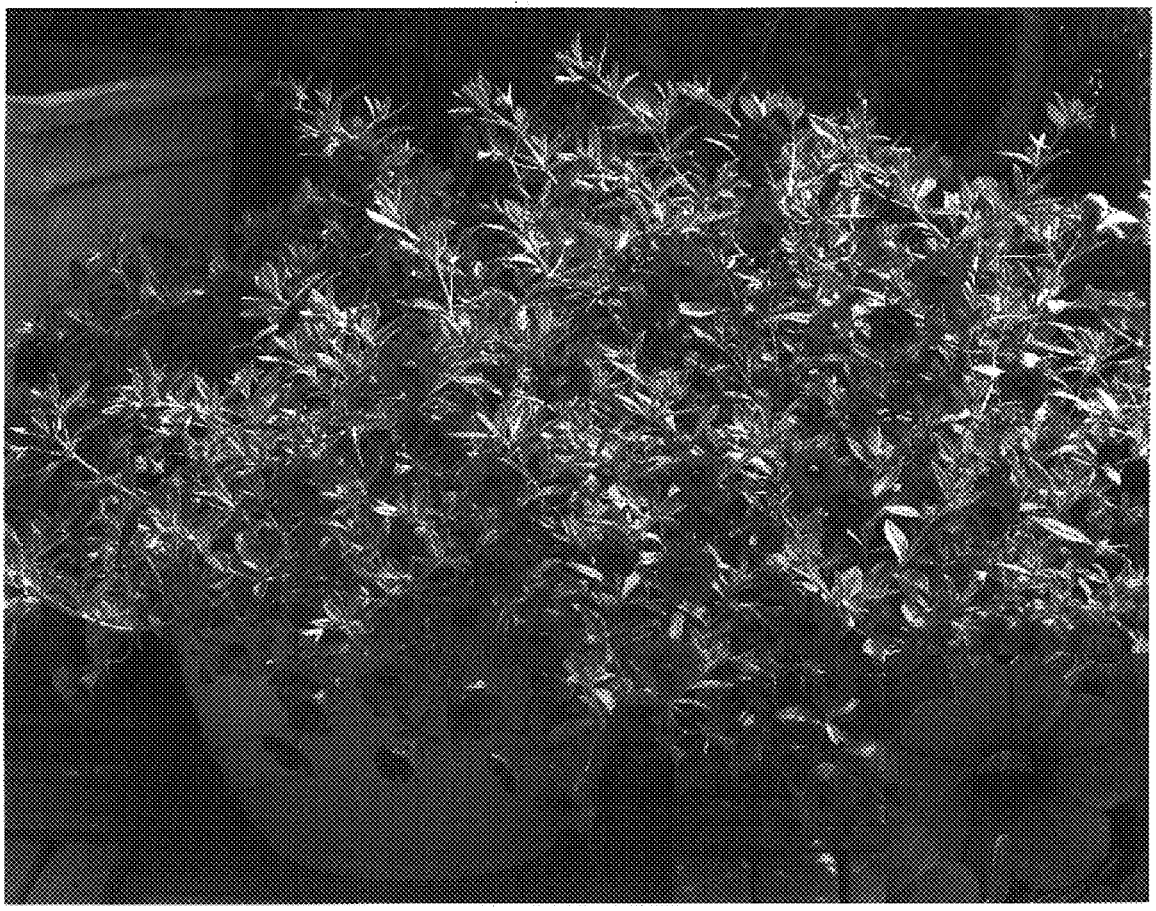

Genus and species: *Calibrochoa* sp.
Variety denomination: 'Cal Britreeda'.

BACKGROUND OF THE INVENTION

The present invention comprises a new and distinct cultivar of *Calibrachoa,* botanically known as *Calibrachoa* sp., and hereinafter referred to by the cultivar name 'Cal Britreeda'. The new cultivar originated from a hybridization made in the year 2001 in Gilroy, Calif. The female parent was proprietary *Calibrachoa* breeding line 44-1 (unpatented) with neon coral flowers. The male parent was proprietary *Calibrachoa* breeding line 252-1 (unpatented) with red flowers.

The new cultivar was created in 2001 in Gilroy, Calif. and has been asexually reproduced over a three-year period by vegetative cuttings and tissue culture in Gilroy, Calif., Andijk, The Netherlands, and Guatemala. The plant has also been trialed at Gilroy, Calif., Litchfield, Mich. and Andijk, The Netherlands. 'Cal Britreeda' has been found to retain its distinctive characteristics through successive asexual propagations. 'Cal Britreeda' reproduces true to type through successive generations of asexual reproduction.

DESCRIPTION OF THE GENUS *CALIBRACHOA* LLAVE & LEX

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* species bear a flower peduncle and three stems. *Petunia* species have a cochlear corolla bud, a single outermost petal which covers the other four, and radially folded and terminally contorted petals. *Calibrachoa* flower buds are flat with all five petals linearly folded with the two lower petals forming a cover around the three other petals and fused together.

DESCRIPTION OF PHOTOGRAPH

This new *Calibrachoa* plant is illustrated by the accompanying photograph which shows blooms, buds, and foliage of the plant; the colors shown are as true as can be reasonably obtained by conventional photographic procedures. The photograph is of a three-month-old plant grown in a lexan-covered greenhouse.

FIG. 1. shows overall plant habit while the inset photograph show a closer view of the mature inflorescence.

DETAILED DESCRIPTION OF THE NEW PLANT

The following detailed descriptions set forth the distinctive characteristics of 'Cal Britreeda'. The data which defines these characteristics were collected from asexual reproductions carried out in Gilroy, Calif. The plant history was taken on four-month-old plants grown in one-gallon pots in a poly-covered greenhouse during the summer season. Color references are primarily to The R.H.S. Colour Chart of The Royal Horticultural Society of London (R.H.S.) (2001). Texture description data were collected by viewing plant parts with a dissecting microscope.

Classification:
*Family.*—Solanaceae.
*Species.*—*Calibrachoa* sp.
Growth:
*Form.*—Semi upright and decumbent.
*Growth and branching habit.*—Good vigorous habit, well branched, full plant.
*Height.*—10–15 cm.
*Width.*—55–65 cm.
*Time to produce a finished flowering plant.*—8–10 weeks.
*Outdoors plant performance.*—Does well in full sun; free flowering through the summer; some heat tolerance; used as a hanging plant or in mixed container.
*Time to initiate and develop roots.*—18–23 days.
*Root description.*—White, fibrous.
Stems:
*Stem color.*—RHS 144A.
*Stem length.*—40–50 cm.
*Stem diameter.*—0.2–0.3 cm.
*Stem internodes length.*—3.0–3.5 cm.
*Stem texture.*—Glandular hairs of various sizes.
*Stem anthocyanin.*—None.
*Peduncle color.*—RHS 148A.
*Peduncle length.*—1.3–1.5 cm.
*Peduncle diameter.*—0.1 cm.
*Peduncle anthocyanin.*—Reddish-purple.
*Peduncle texture.*—Glandular hairs of various sizes.
Leaves:
*Arrangement.*—Alternate; upper leaves sub-opposite.
*Color.*—Upper surface: RHS 137B. Lower surface: RHS 137C.
*Length.*—2.6–2.8 cm.
*Width.*—0.7–0.8 cm.
*Shape.*—Elliptic.
*Margin.*—Entire.
*Apex.*—Obtuse.
*Base.*—Acuminate.
*Texture.*—Gladular hairs.
*Venation.*—Pinnate.
*Venation color.*—RHS 144A.
*Petiole.*—Color: RHS 144A. Length: 0.2–0.3 cm. Width: 0.2 cm. Texture: Glandular hairs.
Flower bud:
*Color at tight bud.*—RHS 184C.
*Bud shape.*—Oblong.
*Bud diameter.*—0.3–0.4 cm.
*Bud length.*—1.9–2.1 cm.
Inflorescence:
*Blooming habit.*—Continuous throughout the growing season. Good floriferousness.
*Inflorescence type.*—Flowers solitary in upper leaf axis.
*Floret type.*—Funnel form, 5 lobed petals, fused at base.
*Flower diameter.*—2.5–2.7 cm.
*Flower depth.*—1.7 cm.
*Lastingness of individual blooms.*—5–8 days.
*Fragrance.*—None.
Flowers:
*Immature flower.*—Color, Upper surface: RHS 46B. Veins: RHS 59A. Diameter: 2.2 cm.
*Mature flower color.*—Upper surface: RHS 47A; RHS 46B at the corolla opening. Main veins: RHS 59B. Secondary veins: RHS 46C. Lower surface: Between RHS 51 C and RHS 51 D. Veins: RHS 176B.
*Corolla.*—Tube color inside: RHS 6A; veins RHS 176C. Tube color outside: RHS 8B. Tube diameter at opening: 0.7 cm Tube length: 1.8 cm. Texture: Glandular hairs various sizes. Shape: Spathulate.
*Petals.*—Apex: Obtuse/Rounded, some are Mucronulate. Base: Fused. Margin: Entire. Waviness of petals: None. Length: 1.1 cm. Width: 1.3 cm. Lobation: Moderate. Texture: Papillose.
*Sepals.*—Number: 5. Color, Lower Surface: RHS 138A. Length: 1.6–1.8 cm. Width: 0.2 cm. Shape: Linear. Apex: Acute to obtuse. Margin: Entire. Texture: Glandular hairs various sizes.
Reproductive organs:
*Stamens.*—5; 2 taller, 3 shorter.
*Filament color.*—RHS 144C.
*Pollen color.*—RHS 7A.
*Pollen amount.*—Moderate.
*Pistil.*—1.
*Pistil length.*—0.8 cm.
*Stigma color.*—RHS 143B.
*Style color.*—RHS 144B.
*Fruit/seed set.*—Not observed.
Disease and insect resistance: Not observed.

COMPARISON WITH KNOWN CULTIVARS

'Cal Bretreeda' differs from the female parent 44-1 (unpatented) by having larger flowers, a red flower color and having more basal branching and a fuller habit than 44-1. 'Cal Britreeda' differs from the male parent 252-1 (unpatented) by having smaller leaves and more center flowering and being earlier to flower than 252-1.

'Cal Britreeda' differs from the commercial variety 'Superbells Red' (U.S. Plant Pat. No. 14,847, designated 'Uscali28' in the patent) by being a little more upright and having longer internodes, and smaller, lighter green leaves than 'Superbells Red'. 'Cal Britreeda' also has larger flowers, with more veining in the petals than 'Superbells Red'.

What is claimed is:

1. A new and distinct *Calibrachoa* plant as shown and described herein.

* * * * *